United States Patent
Honmou et al.

(10) Patent No.: US 9,115,344 B2
(45) Date of Patent: *Aug. 25, 2015

(54) MESENCHYMAL STEM CELL AND A METHOD OF USE THEREOF

(75) Inventors: Osamu Honmou, Sapporo (JP); Kazuo Hashi, Sapporo (JP); Teiji Uede, Sapporo (JP)

(73) Assignees: NC MEDICAL RESEARCH INC., Tokyo (JP); ASKA PHARMACEUTICAL CO., LTD., Tokyo (JP); MITSUI SUMITOMO INSURANCE CARE NETWORK CO., LTD., Tokyo (JP)

(*) Notice: Subject to any disclaimer, the term of this patent is extended or adjusted under 35 U.S.C. 154(b) by 103 days.

This patent is subject to a terminal disclaimer.

(21) Appl. No.: 13/481,180

(22) Filed: May 25, 2012

(65) Prior Publication Data

US 2012/0237486 A1 Sep. 20, 2012

Related U.S. Application Data (60) Division of application No. 13/040,954, filed on Mar. 4, 2011, now abandoned, which is a continuation of application No. 12/076,092, filed on Mar. 13, 2008, now abandoned, which is a continuation of application No. 11/189,050, filed on Jul. 26, 2005, now abandoned, which is a division of application No. 10/330,963, filed on Dec. 23, 2002, now Pat. No. 7,098,027, which is a continuation-in-part of application No. PCT/JP01/05456, filed on Jun. 26, 2001.

(30) Foreign Application Priority Data

Jun. 26, 2000 (JP) ................. 2000-190421
May 29, 2001 (JP) ................. 2001-160579

(51) Int. Cl.
| | |
|---|---|
| A61K 35/12 | (2006.01) |
| C12N 5/00 | (2006.01) |
| C12N 5/0775 | (2010.01) |
| C12N 5/079 | (2010.01) |
| A61K 35/28 | (2015.01) |

(52) U.S. Cl.
CPC .............. *C12N 5/0675* (2013.01); *A61K 35/28* (2013.01); *C12N 5/0622* (2013.01); *C12N 5/0663* (2013.01); *A61K 35/12* (2013.01); *A61K 2035/124* (2013.01); *C12N 2506/1353* (2013.01)

(58) Field of Classification Search
None
See application file for complete search history.

(56) References Cited

U.S. PATENT DOCUMENTS

| | | | |
|---|---|---|---|
| 5,108,759 A | 4/1992 | Ranney | |
| 5,197,985 A | 3/1993 | Caplan et al. | |
| 5,633,283 A | 5/1997 | Kingston et al. | |
| 5,733,542 A | 3/1998 | Haynesworth et al. | |
| 5,811,094 A | 9/1998 | Caplan et al. | |
| 5,986,078 A * | 11/1999 | Garkavtsev et al. | 536/23.1 |
| 6,673,606 B1 | 1/2004 | Tennekoon et al. | |
| 2001/0014670 A1 | 8/2001 | Balin et al. | |
| 2002/0123465 A1 | 9/2002 | Twardzik et al. | |
| 2002/0132343 A1 | 9/2002 | Lum | |
| 2002/0168766 A1 | 11/2002 | Gold et al. | |
| 2003/0161818 A1 | 8/2003 | Weiss et al. | |
| 2004/0259254 A1 | 12/2004 | Honmou et al. | |
| 2005/0169896 A1 | 8/2005 | Li et al. | |
| 2006/0062771 A1 | 3/2006 | Honmou et al. | |
| 2006/0275272 A1 | 12/2006 | Li et al. | |
| 2007/0178591 A1 | 8/2007 | Honmou et al. | |
| 2009/0162327 A1 | 6/2009 | Li et al. | |

FOREIGN PATENT DOCUMENTS

| | | |
|---|---|---|
| WO | 99/43286 | 9/1999 |
| WO | 00/12683 | 3/2000 |
| WO | 00/31545 A1 | 6/2000 |
| WO | 00/69448 A1 | 11/2000 |
| WO | 03/038074 A1 | 5/2003 |
| WO | 03/038075 A1 | 5/2003 |
| WO | 03/038090 A1 | 5/2003 |
| WO | 2005/007176 A1 | 1/2005 |

OTHER PUBLICATIONS

Brandes AA et al. 2001. Changing boundaries in the treatment of malignant gliomas. Expert Rev Anticancer Ther 1: 357-70 (abstract only).*

Greenberg HS et al. 2001. Adult medulloblastoma: Multiagent chemotherapy. Neuro-Oncology 3: 29-34.*

Groothuis DR. 2000. The blood-brain and blood-tumor barriers: A review of strategies for increasing drug delivery. Neuro-Oncology 2: 45-59.*

Ehtesham M et al. 2002. The Use of Interleukin 12-secreting Neural Stem Cells for the Treatment of Intracranial Glioma. Cancer Res 62: 5657-5663.*

Bexell D et al. 2010. Toward Brain Tumor Gene Therapy Using Multipotent Mesenchymal Stromal Cell Vectors. Molecular Therapy 18: 1067-1075.*

Sugita Y et al. 2001. Acute focal demyelinating disease simulating brain tumors: histopathologic guidelines for an accurate diagnosis. Neuropathology 21: 25-31 (abstract only).*

(Continued)

*Primary Examiner* — Lora E Barnhart Driscoll
(74) *Attorney, Agent, or Firm* — Sughrue Mion, PLLC (57) ABSTRACT

Demyelinated axons were remyelinated in the demyelinated rat model by collecting bone marrow cells from mouse bone marrow and transplanting the mononuclear cell fraction separated from these bone marrow cells.

8 Claims, 3 Drawing Sheets

(56) References Cited

OTHER PUBLICATIONS

U.S. Appl. No. 60/134,344, filed May 14, 1999.
Akiyama et al., "Transplantation of Clonal Neural Precursor Cells Derived from Adult Human Brain Establishses Functional Peripheral Myelin in the Rat Spinal Cord," Experimental Neurology, 2001, pp. 27-39, vol. 167, Academic Press, Inc.
Archer et al., "Myelination by Cryopreserved Xenografts and Allografts in the Myelin-Deficient Rat,"Experimental Neurology, 1994, pp. 268-277, vol. 125, Academic Press, Inc.
Armstrong, R.J., et al., Survival, Neuronal Differentiation, and Fiber Outgrowth of Propagated Human Neural Precursor Grafts In An Animal Model of Huntington's Disease. Cell Transplant 2000; 9(1)55-64.
Azizi et al., "Engraftment and Migration of Human Bone Marrow Stromal Cells Implanted in the Brains ofAlbino Rats Similarities to Astrocyte Grafts," Proceedings of The National Academy of Science of USA,Medical Sciences, vol. 95, No. 7, 1998, pp. 3908-3913.
Barker, R.A., Prospects for the Treatment of Parkinson's Disease Using Neural Grafts, Expert Opinion on Pharmacotherapy. 2000 1(5):889-902.
Berkelaar et al, Axotomy Results in Delayed Death and Apoptosis of Retinal Ganglion Cells in Adult Rats, J Neurosci. 1994;14(7):4368-74).
Bianco et al., "Marrow stromal stem cells," J. Clin. Invest., 2000, 105:1663-1668.
Bjartmar, C. et al., "Axonal and neuronal degeneration in multiple sclerosis: mechanisms and functional consequences", Curr Opin Neurol. Jun. 2001; 14(3): 271-8. Abstract.
Bjorklund A et al. 2000. Cell replacement therapies for central nervous system disorders. Nat Neurosci 3: 537-544.
Bjornson et al., "Turning Brain into Blood: A Hematopoietic Fate Adopted by Adult Neural Stem Cells inVivo," Science, 1999, pp. 534-537, vol. 283.
Blakemore et al., "Extensive Oligodendrocyte Remyelination following Injection of Cultured CentralNervous System Cells into Demyelinating Lesions in Adult Central Nervous System," Dev. Neurosci., 1988,pp. 1-11, vol. 10, 1988 S. Karger AG, Basel.
Blakemore, "Remyelination of CNS axons by Schwann cells transplanted from the sciatic nerve,"Nature, 1997, pp. 68-69, vol. 266.
Borlongan CV. Transplantation therapy for Parkinson's disease. Exp Opin Invest Drugs 9: 2319-2330 (2000).
Borlongan, C.V., et al. Cerebral Ischemia and CNS Transplantation: Differential Effects of Grafted Fetal Rat Striatal Cells and Human Neurons Derived From a Clonal Cell Line. Neuroreport. 1998 16;9(16): 3703-9.
Borlongan, C.V.. et al., Neural Transplantation for Neurodegenerative Disorders. Lancet 1999 353 suppl 1; 51:29-30.
Campagnoli et al., "Identification of Mesenchymal Stem/Progenitor Cells in Human First-Trimester Fetal Blood, Liver and Bone Marrow", Blood, Oct. 15, 2001, 2396-2402, 98, 8.
Chalmers-Redman et al., "In Vitro Propagation and Inducible Differentiation of Multipotential ProgenitorCells from Human Fetal Brain," Neuroscience, 1997, pp. 1121-1128, vol. 76, No. 4, 1996 IBRIO,Published by Elsevier Science Ltd, Great Britain.
Chen et al., "Intravenous bone marrow stromal cell therapy reduces apoptosis and promotes endogenouscell proliferation after stroke in femal rat," J. Neurosci. Res., 2003, 73:778-786.
Chen J. et al., Intracerebral transplantation of bone marrow with BDNF after MCAo in rat. Neuropharmacology 2000 39(5):711-6.
Chen J. et al. 2001, Therapeutic Benefit of Intravenous Administration of Bone Marrow Stromal Cells after Cerebral Ischemia in rats. Stroke 32: 1005-1011.
D'Allemand, G., Laboratory Instrumentation, 4 Ed., Haven MC et al., ed., Wiley and Sons, 1995, pp. 31-34.
Deans et al., "Mesenchymal Stem Cells; Biology and Potential Clinical Uses," Experimental Hematology,International Society for Experimental Hematology, Elsevier, vol. 28, 2000, pp. 875-884.
Definitions of "neurology" and "disorder". Webster's College Dictionary (Random House, 1991). pp. 386-387, 909.

Devine et al., "Mesenchymal stem cells distribute to a wide range of tissues following systemic infusioninto nonhuman primates," Blood, 2003, 101:2999-3001.
Devine SM et al. 2001. Mesenchymal stem cells are capable of homing to the bone marrow of non-human primates followingsystemic infusion. Exp Hematol 29: 244-255.
Dinsmore, J.H., Treatment of Neurodegenerative Diseases with Neural Cell Transplantation. Expert Opinion on Investigational Drugs. 1998 7(4): 527-34.
Eglitis, Martin A. et al., "Targeting of Marrow-derived astrocytes to the ischemic brain", NeuroReport 10, 1289-1292 (1999).
Eglitis, Martin A., "Hematopoietic cells differentiate into both microglia and macroglia in the brains of adult mice", Proc. Natl. Acad. Sci. USA, vol. 94, pp. 4080-4085, 1997.
Fink, J.S., et al., Porcine Xenografts in Parkinson's Disease and Huntington's Disease Patients: Preliminary Results. Cell transplantation 2000 9(2)273-8.
Fisher, L. J., Neural Precursor Cells: Applications for the Study and Repair of the Central Nervous System. Neurobiology Disease. 1997;4(1):1-22.
Flax et al., "Engraftable human neural stem cells respond to developmental cues, replace neurons, andexpress foreign genes," Nature Biotechnology, 1998, pp. 1033-1039, vol. 16.
Franklin et al., "Schwan Cell-Like Myelination Following Transplantation of an Olfactory Bulb-Ensheathing Cell Line Into Areas of Demyelination in the Adult CNS," GLIA, 1996, pp. 217-224, vol. 17,1996 Wiley-Liss, Inc.
Freeman, T.B., et al., Transplanted Fetal Striatum in Huntington's Disease: Phenotypic Development and Lack of Pathology. Proc Natl Acad Sci USA. 2000 5;97(25):13877-82.
Fricker-Gates, R.A., et. al., Neural Transplantation: Restoring Complex Circuitry in the Striatum. Restorative Neurology Neuroscience. 2001;19(1-2):119-38.
Gage et al., "Survival and differentiation of adult neuronal progenitor cells transplanted to the adult brain,"Proc. Natl. Acad. ScL USA, 1995, pp. 11879-11883, vol. 92.
Galy et al., "Hematopoietic Progenitor Cells of Lymphocytes and Dendritic Cells," Journal ofImmunotherapy, Lippincott-Raven Publishers, vol. 21, No. 2, 1998, pp. 132-141.
Gao et al., "The dynamic in vivo distribution of bone marrow-derived mesenchymal stem cells afterinfusion," Cells Tissues Organs, 2001, 169:12-20.
Gessani et al., Macrophages, Paulnock DM, ed., Oxford University Press, 2000, p. 45-50.
Gumpel, "Transplantation of Human Embryonic Oligodendrocytes into Shiverer Brain," Annals New YorkAcademy of Sciences, 1987, pp. 71-85, vol. 495.
Haynesworth et al., "Cell Surface Antigens on Human Marrow-Derived Mesenchymal Cells areDetected by Monoclonal Antibodies," Bone, 1992, 13(1):69-80.
Helmuth, Neuroscience. Stem Cells Her Call of Injured Tissue. Science. 2000 24; 290(5496): 1479-810).
Honmou et al., "Restoration of Normal Conduction Properties in Demyelinated Spinal Cord Axons in theAdult Rat by Transplantation of Exogenous Schwann Cells," The Journal of Neuroscience, May 15, 1996, pp. 3199-3208, vol. 16, No. 10, 1996 Society for Neuroscience.
Imaizumi et al., "Transplanted Olfactory Ensheathing Cells Remyelinate and Enhance Axonal Conductionin the Demyelinated Dorsal Columns of the Rat Spinal Cord," The Journal of Neuroscience, Aug. 15, 1998,pos. 6176-6185, vol. 18, No. 16; 1996 Society for Neuroscience.
Javazon et al., "Rat Marrow Stromal Cells are More Sensitive to Plating Density and Expand More Rapidly from Single-Cell-Derived Colonies than Human Marrow Stromal Cells", Stem Cells, 2001, 219-225, 19.
Kato et al., "Transplantation of Human Olfactory Ensheathing Cells Elicits Remyelination of DemyelinatedRat Spinal Cord," GLIA, 2000, pp. 209-218, vol. 30, Wiley-Liss, Inc.
Koc et al., "Allogenic mesenchymal stem cell infusion for treatment of metachromatic leukodystrophy(MLD) and Hurler syndrome (MPS-IH)," Bone Marrow Transplant, 2002, 30(4):215-22.

(56) References Cited

OTHER PUBLICATIONS

Kopen et al., "Marrow stromal cells migrate throughout forebrain and cerebellum, and they differentiateinto astrocytes after injection into neonatal mouse brains," Proc. Natl. Acad. Scl. USA, Sep. 1999,pp. 10711-10716, vol. 96.
Kordower, J.H., et al. Grafts of EGF Responsive Neural Stem Cells Derives From GFAP-Hngf Transgenic Mice: Trophic and Tropic Effects in a Rodent Model of Huntington's Disease. Journal of Comparative Neurology. 1997; 387:96-113.
Kornek, et al, Multiple Sclerosis and Chronic Autoimmune Encephalomyelitis: A Comparative Quantitative Study of Axonal Injury in Active, Inactive, and Remyelinated Lesions, American Journal Pathology 2000, 157: 267-276.
Lane et al., Stromal-Derived Factor 1-Induced Megakaryocyte Migration and Platelet Production isDependent on Matrix Metalloproteinases, Blood, vol. 96, No. 13, pp. 4152-4159, 2000.
Li Y, et al. Intrastriatal Transplantation of Bone Marrow Nonhematopoietic Cells Improves Functional Recovery After Stroke in Adult Mice. J Cereb Blood Flow Metab 2000; 20:1311-1319.
Li, Y, et al. Adult Bone Marrow Transplantation After Stroke in Adult Rats. Cell transplant. 2001 10(1): 31-40.
Liu, Xiao Z. et al, "Neuronal and Glial Apoptosis after Traumatic Spinal Cord Injury", The Journal of Neuroscience, 1997, 17(14): 5395-5406.
Lois et al., "Proliferating subventricular zone cells in the adult mammalian forebrain can differentiate intoneurons and glia," Proc. Natl. Acad. Sci, USA, 1993, pp. 2074-2077, vol. 90.
Lu, Dunyue, et al, "Adult bone marrow stromal cells administered intravenously to rats after traumatic brain injury migrate into brain and improve neurological outcome", Regeneration and Transplantation, vol. 12, No. 3, 2001, pp. 559-563.
MacLeod MA. Potential treatments and treatment strategies in Creutzfeldt-Jakob disease. 2003, IDrugs 6:345-50. Abstract only.
Majumdar et al., "Phenotypic and Function al Comparison of Cultures of Marrow-Derived MesenchymalStem Cells (MSCs) and Stromal Cells," J. Cell. Physiol., Jul. 1998, 176(1):57-66.
Martin, Lee J., Neuronal cell death in nervous system development, disease, and injury (Review), International Journal of Molecular Medicine 7: 455-478, 2001.
Mattson MP. 2000. Emerging neuroprotective strategies for Alzheimer's disease: dietary restriction, telomerase activation, andstem cell therapy. Exp Gerontol 35: 489-502.
Mattson, Mark P., "Apoptosis in Neurodegenerative Disorders", Nature Review, 2000, vol. 1, pp. 120-129.
McCarthy, D.A., Cytometric Analysis of Cell Phenotype and Function, Cambridge University Press, 2001,pp. 20-24 and 222-224.
McDonald, J.W., et al., Transplanted embryonic stem cells survive, differentiate and promote recovery in injured rat spinal cord. Nature Medicine. 1999 5(12):1410-2.
Mezey, Eva, "Bone marrow: a possible alternative source of cells in the adult nervous system", European Journal of Pharmacology 405, (2000) 297-302.
Morshead et al., "Neural Stem Cells in the Adult Mammalian Forebrain: A relatively QuiescentSubpopulation of Subependymal Cells," Neuron, Nov. 1994, pp. 1071-1082, vol. 13, 1994, CellPress.
Moyer et al., "Culture, Expansion, and Transplantation of Human Fetal Neural Progenitor Cells,"ransplantation Proceedings, 1997, pp. 1040-1041, vol. 29, 1997 Elsevier Science Inc.
Noti et al., "Structural and functional Characterization of the Leukocyte Integrin CD//d," The Journal ofBiological Chemistry, The American Society for Biochemistry and Molecular Biology, Inc., vol. 270, No. 12,pp. 8859-8969, 2000.
Oostendorp et al., "VLA-4-Mediated Interactions Between Normal Human Hematopoietic Progenitorsand Stromal Cells," Leukemia and Lymphoma, Harwood Academic Publishers, vol. 24, pp. 423-435, 1997.
Ourednik V., et al. Neural stem cells are uniquely suited for cell replacement and gene therapy in the CNS. Novartis Foundation Symposium. 2000 231:242-62.
Patel et al., Cell Separation: A Practical Approach, 1998, Oxford University Press, pp. 71-73.
Perlow, M.J., Brain Grafting as a Treatment for Parkinson's Disease. Neurosurgery. 1987 20(2):335-42.
Peterson et al. "Inflammation, demyelination, neurodegeneration, and neuroprotection in the pathogenesis of multiple sclerosis", 2007, J Neuroimmunol 184: 37-44.
Peterson, et al, Transected neuritis, apoptotic neurons, and reduced inflammation in cortical multiple sclerosis lesions, Annals of Neurology, 2001; 50: 389-400.
Pittenger et al., "Multilineage Potential of Adult Human Mesenchymal Stem Cells," SupplementaryMaterial for Science, American Association for the Advancement of Science, vol. 284, No. 5411, pp. 143-147, 1999, htto://www.sciencemao.org/feature/data/983855.shl.
Quesenberry et al., "Stromal Cell Regulation of Lymphoid and Myeloid Differentiation," Blood Cells,Springer-Verlag, vol. 13, pp. 137-146, 1987.
Reynolds et al., "Generation of Neurons and Astrocytes from Isolated Cells of the Adult MammalianCentral Nervous System," Sciense, Mar. 27, 1992, pp. 1707-1710, vol. 255.
Rothwell, Nancy et al, "The Role of Interleukin 1 in Acute Neurodegeneration and Stroke: Pathophysiological and Therapeutic Implications", J. Clin. Invest, vol. 100, No. 11, 1997, 2648-2652.
Sasaki et al., "Transplantation of an Acutely Isolated Bone Marrow Fraction Repairs Demyelinated AdultRat Spinal Cord Axons," GLIA, vol. 35, pp. 26-34 (2001).
Shihabuddin, L.S., et al. The search for neural progenitor cells: prospects for the therapy of neurodegenerative disease. Mol Med Today. 1999 5(11): 474-80.
Studer, L., et al. Transplantation of Expanded Mesencephalic Precursors Leads to Recovery in Parkinsonian Rats. Nature Neuroscience 1998 1(14):290-5.
Svendsen et al., "Long-Term Survival of Human Central Nervous System Progenitor Cells Transplantedinto a Rat Model of Parkinson's Disease," Experimental Neurology, 1997, pp. 135-146, vol. 148, 1997Academic Press.
Szilvassy et al., "Differential Homing and Engraftment Properties of Hematopoietic Progenitor CellsFrom Murine Bone Marrow, Mobilized Peripheral Blood and Fetal Liver," Hematopoiesis, (2001) vol. 98, No. 7, pp. 2108-2115.
Takeno et al., "Degeneration of spiral ganglion cells in the chinchilla after inner hair cell loss induced bycarboplatin," Audiology and Neuro-Otology (1998), vol. 3, pp. 281-290.
Thalmeier, Karin, et al., "Mesenchymal Differentiation and Organ Distribution of Established Human Stromal Cell Lines in NOD/SCID Mice", Acta Haematol 2001; 105:159-165.
The BCCA Cancer Drug Manual: entry for thiotepa; www.bccancer.bc.ca/NR/rdonlvres/4AC04698B-EC234D2F-8401-4706E059DC55/9529/Thiotebamonooraph1jul05.pdf; accessed Mar. 16, 2006, 6 pgs.
Thomas et al., Taber's Encyclopedic Medical Dictionary, F.A. Davis Co., 1997, pp. 257, 1168 and 1805.
Trapp, Bruce D. et al, "Neurodegeneration in Multiple Sclerosis: Relationship to Neurological Disability", Neuroscientist 5:48-57, 1999. Abstract.
Turski, Lechoslaw, "ZK200775: A phosphonate quinoxalinedione AMPA antagonist for neuroprotection in stroke and trauma", Proc. Natl. Acad. Sci. USA, vol. 95, pp. 10960-10965, Sep. 1998.
Ugozzioli et al, "Detection of specific alleles by using allele-specific primer extension followed by capture on solid support", GATA, vol. 9(4), pp. 107-112, 1992.
Utzachneider et al., "Transplantationof glial cells enhances action potential conduction of amyelinatedspinal cord axons in the myelin-deficient rat," proc. Natl. Acad. Sci. USA, Jan. 1994, pp. 53-57, vol. 91.
Veizovic, Tina et al., Resolution of Stroke Deficits Following Contralateral Grafts of ConditionallyImmortal Neuroepithelial Stem Cells. Stroke. 2001;32:1012-1019.
Verloes A. et al, Genetic and clinical aspects of lissencephaly, Rev Neurol (Paris), 2007, 163:533-47. Abstract Only.

(56) References Cited

OTHER PUBLICATIONS

Wada R., et al., Microglial activation precedes acute neurodegeneration in Sandhoff disease and is suppressed by bone marrow transplantation. Proc Natl Acad Sci USA. 2000 97(20):10954-9.
Wang, Jih-Shivan, et al., "The coronary delivery of marrow stromal cells for myocardial regeneration: Pathophysiologic and therapeutic implications", The Journal of Thoracic and Cardiovascular Surgery (2001), vol. 122, No. 4, pp. 699-705.
Watt et al., "CD164—A Novel Sialomucin on CD34 Cells," Leukemia and Lymphoma, Harwood AcademicPublishers, vol. 37, Nos. 1-2, pp. 1-25, 2000.
Woodbury et al., "Adult Rat and Human Bone Marrow Stromal Cells Differentiate Into Neurons," Journalof Neuroscience Research, vol. 61, pp. 364-370 (2000).
Yandava et al., ""Global" cell replacement is feasible via neural stem cell transplantation: Evidence from the dysmyelinated shriver mouse brain," Proc. Natl. Acad. Sci, USA, 1999, pp. 7029-7034.
Yin et al, Myelin-Associated Glycoprotein Is a Myelin Signal That Modulates the Caliber of Myelinated Axons, J. Neurosci. 1998; 18: 1953-1962.
Yin et al., "AC133, A Novel Marker for Human Hematopoietic Stem and Progenitor Cells," Blood, vol. 90,No. 12, 1997, pp. 5002-5012.
Yuan, Junying, et al, "Apoptosis in the nervous system", Nature, vol. 407, 2000, pp. 802-809.
Halfpenny, C. et al. "Cell Transplantation, Myelin Repair, and Multiple Sclerosis". 2002, Lancet Neurol 1: 31-40.
Lassmann, H.. "Stem Cell and Progenitor Cell Transplantation in Multiple Sclerosis: The Discrepancy Between Neurobiological Attraction and Clinical Feasibility". 2005, J. Neurol Sci 233: 83-86.
Plews, M et al.. "Factors Affecting the Accuracy of Urine-Based Biomarkers of BSE". 2011, Proteome Sci 9: 6. 11 pages.
Rice CM et al."Autologous bone marrow stem cells—properties and advantages" . 2008, J Neurol Sci 265: 59-62.
Vogel, G. Capturing the Promise of Youth, Science, 1999, 286 (5448): 2238. 4 pages.
Yang J et al. "Cellular Remyelinating Therapy in Multiple Sclerosis". 2009, J Neurol Sci 276: 1-5.
Naegele, Janice R., et al., "Recent advancements in stem cell and gene therapies for neurological disorders and intractable epilepsy," Neuropharmacology, vol. 58, pp. 855-864, 2010.
Shetty, Ashor K., et al., "Concise Review: Prospects of Stem Cell Therapy for Temporal Lobe Epilepsy," Stem Cells, vol. 25, pp. 2396-2407, 2007.
Dennis W. Dickson et al., "Microglia and cytokines in neurological disease, with special reference to AIDS and Alzheimer's disease", GLIA, 1993, 7: 75-83.
Luisa Minghetti et al., "Microglia as effector cells in brain damage and repair: focus on prostanoids and nitric oxide", Progress in Neurobiology, 1998, 54: 99-125.
Xiaohua Xu et al., "Enhancing Central Nervous System Repair—The Challenges", CNS Drugs, 2011, 25(7): 555-573.
Frank Barry et al., "The SH-3 and SH-4 Antibodies Recognize Distinct Epitopes on CD73 from Human Mesenchymal Stem Cells", *Biochemical and Biophysical Research Communications*, 2001, 289: 519-524.
Zhao et al., "Human Bone Marrow Stem Cells Exhibit Neural Phenotypes and Ameliorate Neurological Deficits after Grafting into the Ischemic Brain of Rats", Experimental Neurology, 2002, 174:11-20.
Longa et al., "Reversible Middle Cerebral Artery Occlusion without Craniectomy in Rats", Stroke, Jan. 1989, vol. 20, No. 1, pp. 84-91.
Mokry J. "Experimental Models and Behavioural Tests Used in the Study of Parkinson's Disease", Physiol. Res., 1995, vol. 44, pp. 143-150.
Morris R. "Spatial Localization and Does Not Require the Presence of Local Cues", Learning and Motivation, 1981, vol. 12, pp. 239-260.
Moyer et al., "Culture Expansion, and Transplantation of Human Fetal Neural Progenitor Cells", Transplantation Proceedings, 1997, vol. 29, pp. 2040-2041.

Nakagawa et al., "Persistent and Secondary Adenovirus -Mediated Hepatic Gene Expression Using Adenovirus Vector Containing CTLA4IgG", Hum. Gene Ther., 1998, vol. 9, No. 12, pp. 1739-1745.
Nakamura et al., "Effective Gene Transfer to Human Melanomas via Integrin-Targeted Adenoviral Vectors". Hum. Gene Ther., 2002, vol. 13, pp. 613-626.
Nakamura et al., "Adoptive Immunotherapy with Murine Tumor-specific T Lymphocytes Engineered to Secrete Interfeukin 2", Cancer Research, 1984, vol. 54, No. 22, pp. 5757-5760.
Namba et al., "Evaluation of the Bystander Effect in Experimental Brain Tumors Bearing Herpes Simplex Virus-Thymidine Kinase Gene by Serial Magnetic Resonance Imaging", Hum. Gene Ther., 1996, vol. 7, pp. 1847-1852.
Neumann-Haefelin et al., "Serial MRI After Transient Focal Cerebral Ischemia in Rats", Stroke, 2000, vol. 31, pp. 1965-1973.
Niwa et al., "Efficient selection for high-expression transfectants with a novel eukaryotic vector", Gene, 1991, vol. 108, pp. 193-199.
Nomura et al., "I.V. Infusion of Brain-Derived Neurotrophic Factor Gene-Modified Human Mesenchymal Stem Cells Protects Against Injury in a Cerebral Ischemia Model in Adult Rat", Neuroscience, 2005, vol. 136, pp. 161-169.
Nyberg-Hoffman et al., "Sensitivity and reproducibility in adenoviral infectious titer determination", Nature Medicine, 1997, vol. 3, No. 7, pp. 808-811.
Ohlsson et al., "Environment Influences Functional Outcome of Cerebral Infraction in Rats", Stroke. Apr. 1995, vol. 26, No. 4, pp. 644-649.
Zhao et al., "Human Bone Marrow Stem Cells Exhibit Neural Phenotypes and Ameliorate Neurological Deficits after Grafting into the Ischemic Brain of Rats", Experimental Neurology, 2002, 174: 11-20.
Fernandez et al., Bone Marrow Transplantation, 1997, 20: 265-271.
Supplementary Search Report for European Patent Application No. 04 74 6855 dated May 27, 2009.
Chen et al., "Human Bone Marrow Stromal Cell Cultures Conditioned by Traumatic Brain Tissue Extracts: Growth Factor Production", Journal of Neuroscience Research, vol. 69, No. 5, Aug. 2002, pp. 687-691, XP009004236.
Chen et al., "International Transplantation Of Bone Marrow With BDNF After MCAO In Rat", Neuropharmacology, vol. 39, No. 5, Mar. 2000, pp. 711-716, XP00938486.
Erices a. et al., "Mesenchymal progenitor cells in human umbilical cord blood", British Journal of Hematology 2000, 109, pp. 235-242.
Kuriwaka M. et al., "Isolation of mesenchymal stem cells in cord blood and placental blood, and induction of differentiation of such mesenchymal stem cells", 2002, J. Jpn. Orthop. Assoc. vol. 76, No. 8. page S1052, 2-D-7.
Sanchez-Ramos J. et al., "Adult Bone Marrow Stromal Cells Differentiate Into Neural Cells in Vitro" Experimental Neurology, 2000, vol. 164, pp. 247-256, XP002940451.
Shuji, T. et al., "Cell Separation Technology and Application by a Novel Filter System", Cell vol. 33, No. 11, pp. 436-439, 2001.
Reyes et al., "Purification and ex vivo expansion of postnatal human marrow mesodermal progenitor cells", Blood, 2001, 98(9): 2615-2625.
Tocci et al., "Mesenchymal Stem Cell: Use And Perspectives", The Hematology Journal, 2003, vol. 4, pp. 92-96.
Ukai et al., "Mesenchymal Stem Cells Derived from Peripheral Blood Protects against Ischemia", Journal of Neurotrauma, 2007, 24(3):508-520.
Kennea et al., "Perinatal applications of neural stem cells", Best Practice & Research Clinical Obstetrics and Gynaecology, 2004, 18(6): 977-994.
The Hokkaido Shimbun. "Treatment of cerebral infarction with the patient's own bone-marrow stem cells collected in advance", Sapporo Medical University, Jul. 7, 2003, one page (and English Translation, two pages).
Nakamura, K. et al., "Gene therapy for rat glioma based on mesenchymal stem cell transplantation", Cancer Science, Proceedings $62^{nd}$ Annual Meeting of the Japanese Cancer Association, Sep. 2003, p. 325, 1514-PA.
Paxinos et al., "Bregma, lambda and the Interaural midpoint in sterotaxic surgery with rats of different sex, strain and weight", J. Neurosci, Methods, 1985, vol. 13, pp. 139-143.

(56) References Cited

OTHER PUBLICATIONS

Pluchino et al., "Neurosphere-derived multipotent precursors promote neuroprotection by an Immunomodulatory mechanism", Nature, 2005, vol. 436, pp. 266-271.
Pluchino et al., "Injection of adult neurospheres Induces recovery in a chronic model of multiple sclerosis", Nature, 2003, vol. 422, pp. 688-694.
Prockop et al., "One strategy for cell and gene therapy: Harnessing the power of adult stem cells to repair tissues". PNAS, 2003, vol. 100, Suppl. 1, pp. 11917-11923.
Prockop, D.J. et al., "Marrow Stromat Cells as Stem Cells for Nonhematopoietic Tissues", Science, 1997, vol. 276, pp. 71-74.
Rhines et al., "Local Immunotherapy with Interleukin-2 Delivered from biodegradable Polymer Micropsheres Combined with Interstitial Chemotherapy: A Novel Treatment for Experimental Malignant Glioma", Neurosurgery, 2003, vol. 52, No. 4, pp. 872-880.
Rochefort et al., "Influence of hypoxia on the domiciliation of Mescenchymal Stem Cells after Infusion into rats: possibilities of targeting pulmonary artery remodeling via cells therapies?", Respiratory Research, 2005, vol. 6, No. 125, pp. 1-13.
Sasaki et al., "Protection of Cortcospinal Tract Neurons After Dorsal Spinal Cord Transaction and Engraftment of Olfactory Ensheathing Cells", GLIA, 2006, vol. 53, pp. 352-359.
Staba et al., "Cord-Blood Transplants from Unrelated Donors in Patients with Hurlers Syndrome, "N. Engl. J. Med., 2004, vol. 350, No. 19, pp. 1960-1969.
Takiguchi et al., "CTLA4IgG Gene Delivery Prevents Autoantibody Production and Lupus Nephritis in MRL//pr Mice", Life Sciences, 2000, vol. 66, No. 11, pp. 991-1001.
Tamura et al., "Focal cerebral infarction in the rat: 1. Operative technique and physiological monitorings for chronic model", Brain and Nerve, 1986, vol. 38, No. 8, pp. 747-751.
Tille et al., "Mesenchymal Cells Potentiate Vascular Endothelial growth factor-Induced Angiogensis in Vitro". Experimental Cell Research, 2002, vol. 280, pp. 179-191.
Toma et al., "Human Mesenchymal Stem Cells Differentiate to a Cardiomyocyte Phenotype in the Adult Murine Heart", Circulation, 2002, vol. 105, pp. 93-98.
Tondreau et al., "Mesenchymal Stem Cells Derived from CD133-Positive Cells in Mobilized Peripheral Blood and Cord Blood: Proliferation, Oct. 14, Expression, and Plasticity", Stem Cells, 2005, vol. 23, pp. 1105-1112.
Tsuda et al., "Efficient BMP2 Gene Transfer and Bone Formation of Mesenchymal Stem Cells by a Fiber-Mutant Adenoviral Vector", Mole. Therapy, 2003, vol. 7, No. 3, pp. 354-365.
Villaron et al., "Mesenchymal stem cells are present in peripheral blood and can engraft after allogeneic hematopoietic stem cell transplantation", Haematologica, 2004, vol. 89 No. 12, pp. 14211427.
Willing et al., "Mobilized Peripheral Blood Cells Administered Intravenously Produce Functional Recovery in Stroke", Cell Transplant, 2003, vol. 12, p. 449-454.
Yamauchi et al., "Pre-administration of angiopoietin-1 followed by VEGF induces functional and mature vascular formation in a rabbit Ischemic model", J. Gene Med., 2003, vol. 5, pp. 994-1004.
Zhang et al., "Human bone marrow stromal cell treatment improves neurological functional recovery in EAE mice," Experimental Neurology, 2005, vol. 195, pp. 16-26.
Zvaifler et al., "Mesenchymal precursor cells in the blood of normal individuals," Arthritis Res., 2000, vol. 2, No. 6, pp. 477-488.
Aggarwal et al., "Human mesenchymal stem cells modulate allogeneic immune cell responses", Blood, 2005, vol. 105, No. 4, pp. 1815-1822.
Auner et al., "Evaluation of potential risk factors for early infectious complications after autologous peripheral blood stem cell transplantation in patients with lymphoproliferative diseases", Ann Hematol, 2005, vol. 84, pp. 532-537.
Bang, et al., "Autologous Mesenchymal Stem Cell Transplantation in Stroke Patients", Ann Neurol. vol. 57, pp. 874-882 (2005).
Barker, et al., "Acute Stroke: Evaluation with Serial Proton MR Spectroscopic Imaging", Radiology, vol. 192, pp. 723-732(1994).

Database Medline on STN, (2002), abstract No. 2002333228 & D. Lu et al., "Intravenous administration of human unbilical cord blood reduces neurological deficit in the rat after traumatic brain injury", Cell Transplant, 2002, vol. 11, No. 3, pp. 275-281.
Bederson, et al., "Evaluation of 2, 3, 5-Triphenylterazolium Chloride as a Stain for Detection and Quantification of Experimental Cerebral Infarction in Rats", Stroke, 1986, vol. 17, No. 6, pp. 1304-1308.
Bender et al., "Identification and Comparison of CD34-Positive Cells ad Their Subpopulations From Normal Peripheral Blood and Bone Marrow Using Multicolor Flow Cytometry", Blood, 1991, vol. 77, No. 12, pp. 2591-2596.
Bernstein et al., "Suppression of Human Cytotoxic T Lymphocyte Responses by Adherent Peripheral Blood Leukocytes", Annals New York Academy of Science, 1988, vol. 532, pp. 207-213.
Brown et al., "Factors That Influence the Collection and Enraftment of Allogenic Peripheral-Blood Stem Cells in Patients With Hematologic Malignancies", Journal of Clinical Oncology, 1997, vol. 15, No. 9, pp. 3067-3074.
Chopp et al., "Spinal cord injury in rat: treatment with bone marrow stromal cell transplantation", Neuron Report, 2000, vol. 11, No. 13, pp. 3001-3005.
Dehari, et al., "Enhanced antitumor effect of RGD fiber-modified adenovirus for gene therapy of oral cancer", Cancer Gene Therapy, 2003, vol. 10, pp. 75-85.
Escolar, et al., "Transplantation of Umbilical-cord Blood in Babies with infantile Krabbe's Disease", The New England Journal of Medicine, 2005, vol. 353, No. 20, pp. 2069-2081.
Chen, et al., "Therapeutic benefit of intracerebral transplantation of bone marrow stromal cells after cerebral ischemia in rats", Journal of the Neurological Sciences, 2001, vol. 189, pp. 49-57.
Friedenstein. A. J., "Precursor Cells of Mechanocytes", International Review of Cytology, 1976, vol. 47, pp. 327-359.
Gavrieli. et al., "Identification of Programmed Cell Death in Situ via Specific Labeling of Nuclear DNA Fragmentation", The Journal of Cell Biology, 1992, vol. 119, No. 3, pp. 493-501.
Goto, et al., "GABA Receptor Agonist Promotes Reformation of the Striatonigral Pathway by Transplant Derived from Fetal Striatal Primordia in the Lesioned Striatum", Experimental Neurology, 1997, vol. 147, pp. 503-509.
Hamano, et al., "Angiogenesis Induced by the Implantation of Self-Bone Marrow Cells: A New Material for Therapeutic Angiogenesis", Cell Transplantation, 2000, vol. 9, pp. 439-443.
Hayashi, et al., "Reduction of Ischemic Damage by Application of Vascular Endothelial Growth Factor in Rat Brain After Transient lschemia", Journal of Cerebral Blood Flow and Metabolism, 1998, vol. 18, pp. 887-895.
Hirouchi et al., "Current state on development of neuroprotective agents for cerebral ischemia," Folia Pharmacol. Jpn., 2002, vol. 120, pp. 107-113.
Honma et al., Intravenous infusion of immortalized human mesenchymal stem cells protects against injury in a cerebral ischemia model in adult rat,. Experimental Neurology, 2006, vol. 199, No. 1, pp. 56-66; Epub 2005 Jun. 20, pp. 1-11.
Huss et al., "Evidence of Peripheral Blood-Derived, Plastic-Adherent CD34-/low Hematopoietic Stem Cell Clones with Mesenchymal Stem Cell Characteristics", Stem Cells, 2000. vol. 18, pp. 252-260.
Iihoshi et al., "A therapeutic window for intravenous administration of autologous bone marrow after cerebral Ischemia in adult rats", Brain Research, 2004, vol. 1007, pp. 1-9.
Inoue et al., "Comparative Analysis of Remyelinating Potential of Focal and Intravenous Administration of Autologous Bone Marrow Cells Into the Rat Demyelinated Spinal Cord," GLIA, 2003, vol. 44, pp. 111-118.
Iwadate et at., "Induction of Immunity in Peripheral Tissues Combined with Intracerebral Transplantation of Interleukin 2-producing Cells Eliminates Established Brain Tumors" Cancer Research, 2001, vol. 61, pp. 8769-8774.
Kanegae et al., "Efficient gene activation in mammalian cells by using recombinant adenovirus expressing site-specific Crerecombinase," Nucleic Acids Research, 1995, vol., 23, No., 19, pp. 3816-3821.
Kawano et al., "Ex vivo expansion of human umbilical cord hematopoietic progenitor cells using a coculture system with human

(56) References Cited

OTHER PUBLICATIONS telomerase catalytic subunit (*hTERT*)-transfected human stromal cells," Blood, 2003, vol. 101, No. 2, pp. 532-540.
Keirstead et al., "Polysiaiylated Neural Cell Adhesion Molecule-Positive CNS Precursors Generate Both Oligodenodrocytes and Schwann Cells to Remyelinate the CNS after Transplantation," J. Neurosci., 1999, vol. 19, No. 17, pp. 7529-7536.
Kobune et al., Telomerized human multipotent mesenchymal cells can differentiate into hematopoietic and cobblestone area-supporting cells, Experimental Hematology, 2003, vol. 31, pp. 715-722.
Koc et al., Allogeneic mesenchymal stem cell Infusion for treatment of metachromatic leukodystrophy (MLD) and hurler syndrome (MPS-IH), Bone Marrow Transplantation, 2002, vol. 30, pp. 215-222.
Koc et al., "Rapid Hematopoietic Recovery After Coinfusion of Autologous-Blood Stem Cells and Culture-Expanded Marrow Mesenchymal Stem Cells in Advanced Breast Cancer Patients Receiving High-dose Chemotherapy." J. Clin. Oncol., 2000, vol. 18, pp. 307-316.
Kopen et al., "Marrow stromal cells migrate throughout forebrain and cerebellum, and they differentiate into astrocytes after injection into neonatal mouse brains," Proc. Natl. Acad. Sci., 1999, vol. 96, pp. 10711-10718.
Kurozumi et al., "BDNF Gene-Modified Mesenchymal Stem Cells Promote Functional Recovery and Reduce Infarct Size in the Rat Middle Cerebral Artery Occlusion Model," Molecular Therapy, 2004, vol. 9, No. 2, pp. 189-197.
Akiyama et al., "Transplantation of Clonal Neural Precursor Cells Derived from Adult Human Brain Establishes Functional Peripheral Myelin in the Rat Spinal Cord", Experimental Neurology, 2001, vol. 167, pp. 27-39.
Archer et al., "Myelination by Cryopreserved Xenografts and Allografts in the Myelin-Deficient Rat", Experimental Neurology, 1994, vol. 125, pp. 268-277.
Bjornson et al., "Turning Brain into Blood: A Hematopoietic Fate Adopted by Adult Neural Stem Cells in Vivo", Science, 1999, vol. 283, pp. 534-537.
Blakemore et al., "Extensive Oligodendrocyte Remyelination following Injection of Cultured Central Nervous System Cells into Demyelinating Lesions in Adult Central Nervous System", Dev. Neurosci., 1988, vol. 10, pp. 1-11.
Brown et al., "Factors That Influence the Collection and Enraftment of Allogeneic Peripheral-Blood Stem Cells in Patients With Hematologic Malignancies", Journal of Clinical Oncology, 1997, vol. 15, No. 9, pp. 3067-3074.
Chalmers-Redman et al., "In Vitro Propagation and Inducible Differentiation of Multipotential Progenitor Cells From Human Fetal Brain", Neuroscience, 1997, vol. 76, No. 4, pp. 1121-1128.
Flax et al., "Engraftable human neural stem cells respond to developmental cues, replace neurons, and express foreign genes", Nature Biotechnology, 1998, vol. 16, pp. 1033-1039.
Franklin et al., "Schwann Cell-Like Myelination Following Transplantation of an Olfactory Bulb-Ensheathing Cell Line Into Areas of Demyelination in the Adult CNS", GLIA, 1996, vol. 17, pp. 217-224.
Gage et al., Survival and differentiation of adult neuronal progenitor cells transplanted to the adult brain, Proc. Natl. Acad. Sci., 1995, vol. 92, pp. 11879-11883.
Gumpel et al., "Transplantation of Human Embryonic Oligodendrocytes into Shiverer Brain", Annals New York Academy of Sciences, 1987, vol. 495, pp. 70-85.
Honmou et al., "Restoration of Normal Conduction Properties in Demyelinated Spinal Cord Axons in the Adult Rat by Transplantation of Exogenous Schwann Cells", The Journal of Neuroscience, 1996, vol. 16, pp. 3199-3208.
Imaizumi et al., "Transplanted Olifactory Ensheathing Cells Remyelinate and Enhance Axonal Conduction in the Demyelinated Dorsal Columns of the Rat Spinal Cord", The Journal of Neuroscience, 1998, vol. 18, pp. 6176-6185.
Kato et al., "Transplantation of Human Olfactory Ensheathing Cells Elicits Remyelination of Demyelinated Rat Spinal Cord", GLIA, 2000, vol. 30, pp. 209-218.
Lois et al., "Proliferating subventricular zone cells in the adult mammalian forebrain can differentiate into neurons and glia", Proc. Natl. Acad. Sci., 1993, vol. 90, pp. 2074-2077.
Majumdar et al., "Phenotypic and Functional Comparison of Cultures of Marrow-Derived Mesenchymal Stem Cells (MSCs) and Stromal Cells", J. Cell. Physiol., 1998, vol. 176, pp. 57-66.
Reynolds et al., "Generation of Neurons and Astrocytes from Isolated Cells of the Adult Mammalian Central Nervous System", Science, 1992, vol. 255, pp. 1707-1710.
Sasaki et al., "Transplantation of an Acutely Isolated Bone Marrow Fraction Repairs Demyelinated Adult Rat Spinal Cord Axons", GLIA, 2001, vol. 35, pp. 26-34.
Svendsen et al., "Long-Term Survival of Human Central Nervous System Progenitor Cells Transplanted into a Rat Model of Parkinson's Disease", Experimental Neurology, 1997, vol. 148, pp. 135-146.
Utzschneider et al., "Transplantation of glial cells enhances action potential conduction of amyelinated spinal cord axons in the myelin-deficient rat", Proc. Natl. Acad. Sci., 1994, vol. 91, pp. 53-57.
Yandava, B.D. et al., "'Global' cell replacement is feasible via neural stem cell transplantation: Evidence from the dsymyelinated *shiverer* mouse brain", Proc. Natl. Acad. Sci., 1999, vol. 96, pp. 7209-7034.
Woodbury et al., "Adult Rat and Human Bone Marrow Stromal Cells Differentiate Into Neurons", J. Neurosci. Res., 2000, vol. 61, pp. 364-370.
Mahmood et al., "Intracerebral Transplantation of Marrow Stromal Cells Cultured with Neurotropic factors Promotes functional Recovery in Adult Rats subjected to Traumatic Brain Injury", Journal of Neurotrauma, 2002, 19(12):1609-1617, XP009078495.
Terashima et al., "Cell separation technology and application by a novel filter system", Cell, 2001, 33(11):436-439, with partial English translation, 1 page.
Chen et al., J. et al., "Therapeutic Benefit of Intravenous Administration of Bone Marrow Stromal Cells After Cerebral Ischemia in Rats", Stroke, 2001, vol. 32, pp. 1005-1011.
Chen, Y. et al., "Ischemic rat brain extracts induce human marrow stromal cell growth factor production", 2002, Neuropathology, 22, pp. 275-279.
Morshead, C.M. et al., "Neural Stem Cells in the Adult Mammalian Forebrain: A Relatively Quiescent Subpopulation of Subependymal Cells", Neuron, 1994, vol. 13, pp. 1071-1082.
Blakemore, W.F. et al., "Remyelination of CNS axons by Schwann cells transplanted from the sciatic nerve", Nature, 1977, vol. 266, pp. 68-69.
Akiyama et al., "Remyelination of spaniel cord axons by intravenous delivery of bone marrow cells", Abstracts-Society for Neuroscience, 2001, vol. 27, No. 2, p. 1562.
Keane-Moore et al., "Human mesenchylmal stem cells can be genetically modified to function as antigen presenting cells", Blood, 1998, vol. 92, No. 10, p. 338a, Abstr. 1338.
Lu et al., "Intravenous Administration of Human Umbilical Cord Blood Reduces Neurological Deficit in the Rat After Traumatic Brain Injury", Cell Transplantation, 2002, vol. 11, pp. 275-281.
Akiyama et al., "Remyelination of the Spinal Cord Following Intravenous Delivery of Bone Marrow Cells", Glia, 2002, vol. 39, pp. 229-236.
Chu et al., "Human neural stem cells can migrate, differentiate, and integrate after intravenous transplantation in adult rats with transient forebrain ischemia", Neuroscience Letters, 2003, vol. 343, pp. 129-133.
Mahmood et al., "Treatment of traumatic brain injury in female rats with intravenous administration of bone marrow stromal cells", Neurosurgery, 2001, vol. 49, No. 5, pp. 1196-1204.

\* cited by examiner

MESENCHYMAL STEM CELL AND A METHOD OF USE THEREOF

CROSS-REFERENCE TO RELATED APPLICATION

This application is a Divisional of U.S. patent application Ser. No. 13/040,954, filed Mar. 4, 2011, which is a Continuation of application Ser. No. 12/076,092, filed Mar. 13, 2008, which is a Continuation of application Ser. No. 11/189,050, filed Jul. 26, 2005, now abandoned, which is a Divisional of application Ser. No. 10/330,963, filed Dec. 23, 2002, now U.S. Pat. No. 7,098,027, which is a Continuation-In-Part of PCT/JP01/05456, filed Jun. 26, 2001, the contents of all of which are incorporated herein by reference in their entirety.

TECHNICAL FIELD

The present invention relates to cells derived from bone marrow cells, cord blood cells, or embryonic hepatic tissues that can differentiate into neural cells, and cell fractions containing such cells. It is expected that these cells and cell fractions can be used to treat neurological diseases, particularly in autologous transplantation therapy.

BACKGROUND ART

Transplantation of oligodendrocytes (i.e., oligodendroglia) (Archer D. R., et al., 1994. Exp. Neurol. 125:268-77; Blakemore W. F., Crang A. J., 1988. Dev. Neurosci. 10:1-11; Gumpel M., et al. 1987. Ann. New York Acad. Sci. 495:71-85) or myelin-forming cells, such as Schwann cells (Blakemore W. F., 1977. Nature 266:68-9; Blakemore W. F., Crang A. J., 1988. Dev. Neurosci. 10:1-11; Honmou O. et al., 1996. J. Neurosci. 16:3199-208), or olfactory ensheating cells (Franklin R. J. et al., 1996. Glia 17:217-24; Imaizumi T. et al., 1998. J. Neurosci. 18(16):6176-6185; Kato T. et al., 2000. Glia 30:209-218), can elicit remyelination in animal models and recovery of electrophysiological function (Utzschneider D. A. et al., 1994. Proc. Natl. Acad. Sci. USA. 91:53-7; Honmou O. et al., 1996. J. Neurosci. 16:3199-208). It is possible to prepare such cells from patients or other persons for cell therapy. However, this method is considerably problematic because tissue material must be collected from either the brain or nerves.

Neural progenitor cells or stem cells derived from brain have the ability to self-renewal and differentiate into various lineages of neurons and glia cells (Gage F. H. et al., 1995. Proc. Natl. Acad. Sci. USA. 92:11879 83; Lois C., Alvarez-Buylla A., 1993. Proc. Natl. Acad. Sci. USA. 90:2074-7; Morshead C. M. et al., 1994. Neuron 13:1071-82; Reynolds B. A., Weiss S., 1992. Science 255:1707-10).

By transplantation into newborn mouse brain, human neural stem cells collected from fetal tissues differentiate into neurons and astrocytes (Chalmers-Redman R. M. et al., 1997. Neurosci. 76:1121-8; Moyer M. P. et al., 1997. Transplant. Proc. 29:2040-1; Svendsen C. N. et al., 1997. Exp. Neurol. 148:135-46), and myelinate the axons (Flax J. D. et al., 1998. Nat. Biotechnol. 16:1033-9). Remyelination and recovery of impulse conduction upon transplantation of neural progenitor (stem) cells derived from adult human brain into demyelinated rodent spinal cord have been reported (Akiyama Y. et al., 2001. Exp. Neurol.).

These studies have evoked great interest due to the indicated possibility of the application of the above-mentioned cells to regenerative strategy of neurological diseases (Akiyama Y. et al., 2001. Exp. Neurol.; Chalmers-Redman R. M. et al., 1997. Neurosci. 76:1121-8; Moyer M. P. et al., 1997. Transplant. Proc. 29:2040-1; Svendsen C. N. et al., 1997. Exp. Neurol. 148:135-46; Yandava B. D. et al., 1999. Proc. Natl. Acad. Sci. USA. 96:7029-34). However, in order to establish cell transplantation therapy (including autologous transplantation) using these cells, still problems, such as establishment of harvest method and requirement of cell expansion using trophic factors, remain to be solved.

According to the recent studies, neural stem cells were revealed to be able to differentiate or transform into hematopoietic cells in vivo, suggesting that neural progenitor (stem) cells are not restricted to the neural cell lineage (Bjornson C. R. et al., 1999. Science 283:534-7). Furthermore, bone marrow stromal cells (not mesenchymal stem cells in the bone marrow) are reported to differentiate into astrocytes by the injection into the lateral ventricles of neonatal mice (Kopen G. C. et al., Proc. Natl. Acad. Sci. USA. 96:10711-6), and into neurons in vitro when cultured under appropriate cell culture conditions (Woodbury D. et al., 2000. J. Neurosci. Res. 61:364-70).

DISCLOSURE OF THE INVENTION

The present inventors have previously isolated and cultured neural stem cells from adult human brain, and established some cell lines. By studying their functions, the inventors newly discovered that the neural stem cells have pluripotency and the ability to self-renewal. Specifically, single-cell expansion of neural progenitor (stem) cells obtained from adult human brain was conducted to establish cell lines; the established cells were then subjected to in vitro clonal analysis. The result showed that the cell lines had pluripotency (namely, differentiation into neuron, astroglia (or astrocyte), and oligodendroglia (i.e., oligodendrocyte)) and the ability to self-renewal (namely, proliferation potency). Thus, these cells were confirmed to possess the characteristics of neural stem cell.

Transplantation of these cells indeed resulted in very favorable graft survival, migration, and differentiation in cerebral ischemic model rats or injury model rats. Furthermore, transplantation of the cells was found to result in functional myelin sheath formation in spinal cord demyelination model rats. Thus, such transplantation allows remyelination of the demyelinated axon and restoration of the neural function in the rat spinal cord demyelination model. Effectiveness of such transplantation therapy using these cells was confirmed by histological, electrophysiological, and behavior studies.

Judging from the above-described findings, transplantation of cultured neural stem cells, which have been isolated from a small amount of neural tissue collected from the cerebrum of a patient, into the lesion of the brain or the spinal cord of the patient seems to be a widely applicable in autotransplantation therapy.

However, while not causing neurologic deficits, collecting tissues containing neural stem cells from cerebrum is relatively invasive. Thus, considering the need for establishing therapeutic methods for various complicated diseases in the nervous system today, it is crucial to establish a safer and simpler method for autotransplantation therapy.

Thus, an objective of the present invention is to provide cellular material that is useful in the treatment of neurological diseases, and which can be prepared safely and readily. Another objective of the present invention is to provide a method for treating neurological diseases, preferably a method for autotransplantation therapy, using the cellular material.

In view of the existing state as described above, to establish donor cells the present inventors focused on the technique of collecting bone marrow cells from bone marrow, a simpler technique as compared to the collection of neural stem cells and routinely used in today's medical practice. First, they collected bone marrow cells from mouse bone marrow, isolated mononuclear cell fraction, and then transplanted this fraction as donor cells into spinal cord demyelination model rats. Surprisingly, it was discovered that the demyelinated axon gets remyelination by the treatment. Hence, the present inventors newly revealed that the mononuclear cell fraction prepared from bone marrow cells have the ability to differentiate into neural cells. The present inventors also discovered that cell fractions containing mesodermal stem cells, mesenchymal stem cell, stromal cells, and AC133-positive cells, that were isolated from the mononuclear cell fraction had the ability to differentiate into neural cells. Besides bone marrow cells, these cell fractions can also be prepared from cord blood cells. Furthermore, AC133-positive cells can be prepared from embryonic hepatic tissues.

Thus, the present invention provides cell fractions containing cells capable of differentiating into neural cells, which are isolated from bone marrow cells, cord blood cells, and embryonic hepatic tissues.

In another embodiment, such cell fractions contain mesenchymal stem cells having the following character: SH2(+), SH3(+), SH4(+), CD29(+), CD44(+), CD14(−), CD34(−), and CD45(−).

In another embodiment, such cell fractions contain stromal cells having the following characteristics: Lin(−), Sca-1(+), CD10(+), CD11D(+), CD44(+), CD45(+), CD71(+), CD90 (+), CD105(+), CDW123(+), CD127(+), CD164(+), fibronectin (+), ALPH(+), and collagenase-1(+).

In another embodiment, such cell fractions contain cells having the character AC133(+).

In addition, the present invention provides cells capable of differentiating into neural cells, which are contained in the above-mentioned cell fraction.

Furthermore, the present invention provides compositions for treating neurological disease, which contain the above-mentioned mononuclear cell fractions or the above-mentioned cells. According to a preferred embodiment of the present invention, the neurological disease is selected from the group consisting of: central and peripheral demyelinating diseases; central and peripheral degenerative diseases; cerebral apoplexy (cerebral infarction, cerebral hemorrhage, subarachnoid hemorrhage); brain tumor; dysfunction of higher function of the brain (the term "higher function of the brain" involves the cognitive function, short and long memory, speech, etc.); psychiatric diseases; dementia; infectious diseases; epilepsy; traumatic neurological diseases; and infarction of spinal cord diseases.

Furthermore, the present invention provides therapeutic methods for neurological diseases, which comprises transplanting of the above-mentioned mononuclear cell fractions, cells, or compositions. In preferred embodiments, the donor cells are derived from a recipient.

The present invention provides mononuclear cell fractions isolated from bone marrow cells, cord blood cells, or embryonic hepatic tissues, wherein the fractions contain cells capable of differentiating into neural cells. It is unclear whether the differentiation of cells contained in the cell fractions provided by the present invention into neural cells is caused by the transformation of so-called hematopoietic cells into neural cells, or, alternatively, by the differentiation of immature cells capable of differentiating into neural cells that are comprised in bone marrow cells, etc. However, the majority of the cells differentiating into neural cells are assumed to be stem or precursor cells, namely, cells having the self-renewal ability and pluripotency. Alternatively, the cells differentiating into neural cells may be stem or precursor cells which have differentiated to some extent into endoderm or mesoderm.

Cells in a cell fraction of the present invention do not have to be proliferated with any trophic factors (then again they can proliferate in the presence of trophic factors). Thus, these cells are simple and practical from the standpoint of the development of autotransplantation technique for the diseases in the neural, and are very beneficial in medical industry. In general, a cell fraction of the present invention is derived from vertebrate, preferably from mammal (for example, mouse, rat, human, etc.).

A cell fraction of the present invention can be prepared by subjecting bone marrow cells or cord blood cells collected from vertebrate to density-gradient centrifugation at 2,000 rpm in a solution for a sufficient time ensuring separation depending on specific gravity, and then recovering the cell fraction with a certain specific gravity within the range of 1.07 to 1.1 g/ml. Herein, the phrase "a sufficient time ensuring separation depending on specific gravity" refers to a time sufficient for the cells to shift to a position in the solution according to their specific gravity, which is typically about 10 to 30 minutes. The specific gravity of the cell fraction to be recovered is within the range of 1.07 to 1.08 g/ml (for example, 1.077 g/ml). Solutions, such as Ficoll solution and Percoll solution, can be used for the density-gradient centrifugation, but is not limited thereto.

Specifically, first, bone marrow (5 to 10 μl) collected from a vertebrate is combined with a solution (2 ml L-15 plus 3 ml Ficoll), and then centrifuged at 2,000 rpm for 15 minutes to isolate a mononuclear cell fraction (approx. 1 ml). The mononuclear cell fraction is combined with culture solution (2 ml NPBM) to wash the cells, and then the cells are again centrifuged at 2,000 rpm for 15 minutes. Then, the precipitated cells are recovered after the removal of the supernatant. Besides femur, sources to obtain a cell fraction of the present invention include sternum, and ilium constituting the pelvis. Any other bone can serve as a source so long as it is large enough. A cell fraction of the present invention can also be prepared from bone marrows and cord blood stored in bone marrow bank or cord blood bank.

Another embodiment of cell fractions of the present invention includes a mononuclear cell fraction isolated and purified from bone marrow cells or cord blood cells, which contains mesodermal (mesenchymal) stem cells capable of differentiating into neural cells. The term "mesodermal (mesenchymal) stem cell" refers to cells that can copy (divide and proliferate) cells with the same potential as themselves and that are capable of differentiating into any type of cells constituting mesodermal (mesenchymal) tissues. Mesodermal (mesenchymal) cells indicate cells constituting tissues that are embryologically categorized to the mesoderms, including blood cell's. The mesodermal (mesenchymal) stem cell includes, for example, cells characterized by SH2 (+), SH3 (+) SH4(+), CD29(+), CD44 (+), CD14(−), CD34 (−), and CD45 (−). A cell fraction containing mesodermal (mesenchymal) stem cells can be obtained, for example, by selecting cells having a cell surface marker, such as SH2, as described above from the above-mentioned cell fraction obtained by centrifuging bone marrow cells or cord blood cells (the cell fraction according to claim 2).

Furthermore, a cell fraction containing mesodermal (mesenchymal) stem cells capable of differentiating into neural cells can be prepared by subjecting bone marrow cells or cord blood cells collected from vertebrate to density-gradient centrifugation at 900 G in a solution for a sufficient time ensuring separation depending on specific gravity, and then recovering the cell fraction with a certain specific gravity within the range of 1.07 to 1.1 g/ml. Herein, "a sufficient time ensuring separation depending on specific gravity" refers to a time sufficient for the cells to shift to a specific position corresponding to their specific gravity in the solution for density-gradient centrifugation, which is typically about 10 to 30 minutes. The specific gravity of a cell fraction to be recovered varies depending on the type of animal (for example, human, rat, and mouse) from which the cells have been derived. A solution to be used for density-gradient centrifugation includes Ficoll solution and Percoll solution, but is not limited thereto.

Specifically, first, bone marrow (25 ml) or cord blood collected from vertebrate is combined with an equal volume of PBS solution, and then centrifuge at 900 G for 10 minutes. Precipitated cells are mixed with PBS and then are recovered (cell density=approx. $4 \times 10^7$ cells/ml) to remove blood components. Then, a 5-ml aliquot thereof is combined with Percoll solution (1.073 g/ml), and centrifuged at 900 G for 30 minutes to extract a mononuclear cell fraction. The extracted mononuclear cell fraction is combined with a culture solution (DMEM, 10% FBS, 1% antibiotic-antimycotic solution) to wash the cells, and is centrifuged at 2,000 rpm for 15 minutes. Finally, the supernatant is removed, precipitated cells are recovered and cultured at 37° C. under 5% $CO^2$ atmosphere.

Another embodiment of a cell fraction of the present invention is a fraction of mononuclear cells isolated from bone marrow cells or cord blood cells, which contains stromal cells capable of differentiating into neural cells. Examples of stromal cell include cells characterized by Lin(−), Sca-1(+), CD10(+), CD11D(+), CD44(+), CD45(+), CD71(+), CD90 (+), CD105(+), CDW123(+), CD127(+), CD164(+), fibronectin (+), ALPH(+), and collagenase-1(+). A cell fraction containing stromal cells can be prepared, for example, by selecting cells having a cell surface marker, such as Lin as described above, from the above-mentioned cell fraction obtained by centrifuging bone marrow cells or cord blood cells (the cell fraction according to claim 2).

Furthermore, such a cell fraction can be prepared by subjecting bone marrow cells or cord blood cells collected from vertebrate to density-gradient centrifugation at 800 G in a solution for a sufficient time ensuring separation depending on specific gravity, and then recovering the cell fraction with a certain specific gravity within the range of 1.07 to 1.1 g/ml. Herein, "a sufficient time ensuring separation depending on the specific gravity" indicates a time sufficient for the cells to shift to a specific position corresponding to their specific gravity in the solution for density-gradient centrifugation, which is typically about 10 to 30 minutes. The specific gravity of a cell fraction to be recovered is preferably within the range of 1.07 to 1.08 g/ml (for example, 1.077 g/ml). A solution to be used for density-gradient centrifugation includes Ficoll solution and Percoll solution, but is not limited thereto.

Specifically, first, bone marrow or cord blood collected from vertebrate is combined with an equal volume of a solution (PBS, 2% BSA, 0.6% sodium citrate, and 1% penicillin-streptomycin). A 5-ml aliquot thereof is combined with Ficoll+Paque solution (1.077 g/ml) and centrifuged at 800 G for 20 minutes to obtain a mononuclear cell fraction. The mononuclear cell fraction is combined with a culture solution (Alfa MEM, 12.5% FBS, 12.5% horse serum, 0.2% i-inositol, 20 mM folic acid, 0.1 mM 2-mercaptoethanol, 2 mM L-glutamine, 1 hydrocortisone, 1% antibiotic-antimycotic solution) to wash the cells, and then are centrifuged at 2,000 rpm for 15 minutes. The supernatant is removed after centrifugation. The precipitated cells are collected and then cultured at 37° C. under 5% $CO^2$ atmosphere.

Another embodiment of a cell fraction of the present invention is a mononuclear cell fraction containing cells characterized by AC133(+) capable of differentiating into neural cells, which is isolated from bone marrow cells, cord blood cells, or embryonic hepatic tissues. Such a cell fraction can be obtained, for example, by selecting cells having a cell surface marker including the above-mentioned AC133(+) from the cell fraction obtained, as described above, by centrifuging bone marrow cells or cord blood cells (the cell fraction according to claim 2).

Furthermore, the cell fraction can be obtained by subjecting embryonic hepatic tissues collected from vertebrate to density-gradient centrifugation at 2,000 rpm in a solution for a sufficient time ensuring separation depending on specific gravity, recovering a cell fraction within the range of a specific gravity of 1.07 to 1.1 g/ml, and then recovering cells with the characteristic of AC133(+) from the cell fraction. Herein, "a sufficient time ensuring separation depending on specific gravity" indicates a time sufficient for the cells to shift to a specific position corresponding to their specific gravity in the solution for density-gradient centrifugation, which is typically about 10 to 30 minutes. The solution to be used for density-gradient centrifugation includes Ficoll solution and Percoll solution, but is not limited thereto.

Specifically, first, liver tissue collected from vertebrate is washed in L-15 solution, and then treated enzymatically in an L-15 solution containing 0.01% DNaseI, 0.25% trypsin, and 0.1% collagenase at 37° C. for 30 minutes. Then, the tissue is dispersed into single cells by pipetting. The single-dispersed embryonic hepatic cells are centrifuged by the same procedure as described for the preparation of the mononuclear cell fraction from femur in Example 1 (1). The cells thus obtained are washed, and then AC133(+) cells are collected from the washed cells using an AC133 antibody. Thus, cells capable of differentiating into neural cells can be prepared from embryonic hepatic tissues. The antibody-based recovery of AC133 (+) cells can be achieved using magnetic beads or a cell sorter (FACS, etc.).

Transplantation of any of these cell fractions containing mesodermal stem cells, mesenchymal stem cells, stromal cells, or AC133-positive cells into demyelinated spinal cord can lead to efficient remyelination of the demyelinated region. In particular, the above-mentioned cell fraction containing mesenchymal stem cells can engraft favorably and differentiate into neural cells such as neurons or glia when transplanted into a stroke model or a cerebral infarction model.

The present invention also provides cells capable of differentiating into neural cells, which are contained in the above-mentioned cell fraction. These cells include, for example, neural stem cells, mesodermal stem cells, mesenchymal stem cells, stromal cells, and AC133-positive cells which are contained in the above-mentioned cell fraction, but are not limited thereto so long as they can differentiate into neural cells.

The present invention also provides compositions for treating neurological diseases, which comprise a cell fraction or cells of the present invention. It is possible to transplant the cell fractions or cells of the present invention without modification. However, in order to improve the efficiency of therapy, they may be transplanted as compositions combined with various additives or introduced with genes. The preparation of compositions of the present invention may comprise, for example, (1) addition of a substance that improves the proliferation rate of cells included in a cell fraction of the present invention or enhances the differentiation of the cells into neural cells, or introducing a gene having the same effect; (2) addition of a substance that improves the viability of cells in a cell fraction of the present invention in damaged neural tissues, or introducing a gene having the same effect; (3) addition of a substance that inhibits adverse effects of damaged neural tissue on the cells in a cell fraction of the present invention, or introducing a gene having the same effect; (4) addition of a substance that prolongs the lifetime of donor cells, or introducing a gene having the same effect; (5) addition of a substance that modulates the cell cycle, or introducing a gene having the same effect; (6) addition of a substance to suppress the immunoreaction or inflammation, or introducing a gene having the same effect; (7) addition of a substance that enhances the energy metabolism, or introducing a gene having the same effect; (8) addition of a substance that improves the migration of donor cells in host tissues, or introducing a gene having the same effect; (9) addition of a substance that improves blood flow (including inductions of angiogenesis), or introducing a gene having the same effect; (10) addition of a substance that cure the infectious diseases, or introducing a gene having the same effect, or (11) addition of a substance that cure the tumors, or introducing a gene having the same effect, but is not limited thereto.

It is considered that the cells according to the present invention are immobilized in the bone marrow by a distinct mechanism involving a certain type of substance (proteins, etc.) and do not normally move out into the peripheral blood. Therefore, to make these cells enter the peripheral blood circulation, conventionally, they are removed from the bone marrow, and then administered intravenously. However, the studies conducted by the present inventors gradually elucidated the mechanism of immobilization of these cells in the bone marrow. The discovery made by the present inventors showed that these cells, which had been localized in the bone marrow, could be made to move out into the peripheral blood by intravenous injection of active factors, such as an antibody, a cytokine, chemicals, or a growth factor. That is, therapeutic effect of bone marrow transplantation that is similar to that of the aforementioned method can be expected from intravenous injection of an active factor, such as an antibody, a cytokine, chemicals, or a growth factor.

A cell fraction, cell, and composition of the present invention can be used for treating neurological diseases. Target neurological diseases for the therapy include, for example, central and peripheral demyelinating diseases; central and peripheral degenerative diseases; cerebral apoplexy (including cerebral infarction, cerebral hemorrhage, and subarachnoid hemorrhage); cerebral tumor; disorders of higher brain function including dementia; psychiatric diseases; epilepsy; traumatic neurological diseases (including head injury, cerebral contusion, and spinal cord injury); infectious diseases; and infarction of spinal cord, but are not limited thereto.

According to the present invention, cells derived from bone marrow cells of a recipient can be transplanted as donor cells (autotransplantation therapy). This has the following advantages: (1) low risk of rejection for the transplantation; and (2) no difficulty in using immunosuppressant. When autotransplantation therapy is arduous, then cells derived from other person or nonhuman animal may be used. Cells frozen for storage are also usable. The donor cells may be derived from cord blood.

Bone marrow can be collected, for example, by anesthetizing (by local or systemic anesthesia) an animal (including human) that serves as a source, put a needle into the sternum or iliac of the animal, and aspirating the bone marrow with a syringe. On the other hand, it is an established technique to collect cord blood at birth by putting needle directly into the umbilical cord, and aspirating the blood from the umbilical cord using syringe, and to store the blood.

Transplantation of cells into a patient can be performed, for example, by first filling a syringe with cells to be transplanted. Herein, the cells are suspended in an artificial cerebrospinal fluid or physiological saline. Then, the damaged neural tissue is exposed by surgery, and, with a needle, directly injecting the cells into the lesion. Due to high migrating potential of cells contained in a cell fraction of the present invention, they can migrate in the neural tissues. Hence, cells can be transplanted into a region adjacent to the lesion. Moreover, injection of the cells into the cerebrospinal fluid is also expected to be efficacious. In the case of the injection of the cells into the cerebrospinal fluid, the cells can be injected into a patient by typical lumbar puncture, without surgical operation only under local anesthetization. Thus, the patient can be treated in patient's sickroom (not in an operation room), which makes the method preferable. Alternatively, intravenous injection (including any systemic transplantations such as intravenous, intraarterial, selective intraarterial administration) of the cells is also expected to be effective. Thus, transplantation can be carried out by a procedure based on typical blood transfusion, which is advantageous in that the treatment can be performed in patient's sickroom.

Furthermore, due to their high migrating potential, cells in a cell fraction of the present invention can be used as a carrier (vector) for genes. For example, the cells are expected to be useful as a vector for gene therapy for various neurological diseases such as brain tumor.

BRIEF DESCRIPTION OF THE DRAWINGS

FIG. 1 shows optical light micrographs of transections of dorsal column of the spinal cord, which had been prepared at 1-mm intervals. (A), normal axon; and (C), damaged demyelinated axon. Patterns of dorsal column observed at higher magnification are shown in (B) for normal axon and in (D) for demyelinated axon. Scale bars: 250 µm in (A) and (C); 10 µm in (B) and (D).

FIG. 2 shows microphotographs demonstrating the remyelination of rat spinal cord (A), after transplantation of adult mouse bone marrow cells; and (C), after transplantation of Schwann cells. Photomicrographs demonstrating remyelinated axon observed at higher magnification are shown in (B), after transplantation of bone marrow cells; and (D), after transplantation of Schwann cells. Scale bars: 250 µm in (A) and (C); 10 µm in (B) and (D).

FIG. 3 shows an electron micrograph of remyelinated axon after the transplantation of bone marrow into the dorsal columns. The tissue was treated with substrate X-Gal to detect transplanted bone marrow cells containing the β-galactosidase gene in the damaged tissues (the reaction product is indicated with arrow). When observed at higher magnification, basal lamina was found around the fibers (wedge-shaped mark; scale bar 1 µm). The presence of large cytoplasmic and nuclear regions and basal lamina in the transplanted cells indicates peripheral myelination.

BEST MODE FOR CARRYING OUT THE INVENTION

The present invention will be described in more detail below with reference to examples based on specific experiments.

EXAMPLE 1

Preparation of Bone Marrow Cells and Schwann Cells (1) Bone Marrow Mononuclear Cells Mouse bone marrow cells (10 μl) were obtained from the femur of adult LacZ (a structural gene of β-galactosidase) transgenic mice (The Jackson Laboratory, Maine, USA). The collected sample was diluted in L-15 medium (2 ml) containing 3 ml Ficoll, and centrifuged at 2,000 rpm for 15 minutes. Cells were collected from the mononuclear cell fraction, and suspended in 2 ml serum-free medium (NPMM: Neural Progenitor cell Maintenance Medium). Following centrifugation (2,000 rpm, 15 min), the supernatant was removed, and precipitated cells were collected and re-suspended in NPMM.

(2) Schwann Cells

Primary Schwann cell cultures were established from the sciatic nerve of neonatal mouse (P1-3) according to the method of Honmou et al. (J. Neurosci., 16(10): 3199-3208, 1996). Specifically, cells were released from sciatic nerve by enzymatic and mechanical treatment. $8 \times 10^5$ cells per plate were plated onto 100-$mm^2$ poly (L-lysine)-coated tissue culture plates and the cells were cultured in Dulbecco's modified Eagle's medium (DMEM) supplemented with 10% (vol/vol) fetal calf serum.

EXAMPLE 2

Experimental Animal Preparation and Transplantation (1) Preparation of Demyelinated Rat Model Experiments were performed on 12 week old Wistar rats. A localized demyelinated lesion was created in the dorsal columns using X-ray irradiation and ethidium bromide injection (EB-X treatment). Specifically, rats were anesthetized with ketamine (75 mg/kg) and xylazine (10 mg/kg) i.p., and a surface dose of 40 Grays of X-ray was irradiated using Softex M-150 WZ radiotherapy machine (100 kV, 1.15 mA, SSD 20 cm, dose rate 200 cGy/min) on the spinal cord caudal to the tenth thoracic spine level (T-10) through a 2×4 cm opening in a lead shield (4 mm thick). Three days after X-ray irradiation, rats were anesthetized as above, and aseptic laminectomy of the eleventh thoracic spine (T-11) was conducted. A demyelinating lesion was generated by the direct injection of ethidium bromide (EB) into the dorsal columns via a glass micropipette whose end was drawn. 0.5 μl saline containing 0.3 mg/ml EB was injected at the depths of 0.7 and 0.4 mm.

(2) Transplantation of Stem or Progenitor Cells that can differentiate or Transform into the Neural Lineages 3 days after the EB injection, 1 μl of the cell suspension ($1 \times 10^4$ cells/pa), which was obtained in Example 1, was injected into the middle of the EB-X-induced lesion. Transplanted rats were immunosuppressed with cyclosporin A (10 mg/kg/day).

EXAMPLE 3

Histological Examination

Rats were deeply anesthetized by the administration of sodium pentobarbital (60 mg/kg, i.p.), and perfused through the heart cannula, first, with phosphate-buffer solution (PBS) and then with a fixative containing 2% glutaraldehyde and 2% paraformaldehyde in 0.14 M Sorensen's phosphate buffer, pH 7.4. Following in situ fixation for 10 minutes, the spinal cord was carefully excised, cut into 1 mm segments and kept in fresh fixative. The tissue was washed several times in Sorensen's phosphate buffer, post-fixed in 1% $OsO_4$ for 2 hours at 25° C., dehydrated by elevating the concentration of the ethanol solution, passed through propylene oxide and embedded in EPON. Then, the tissue was cut into sections (1 μm), counterstained with 0.5% methylene blue and 0.5% azure II in 0.5% borax, and examined under light microscope (Zeiss: Axioskop FS). Ultrathin sections were counterstained with uranyl and lead salts, and examined with JEOL JEM1200EX electron microscope (JEOL, Ltd., Japan) at 60 kV.

A 50×50 μm standardized region in the central core of the dorsal columns in the spinal cords near the site wherein the cells were initially injected was used for morphometric analysis. The numbers of remyelinated axons and cell bodies associated with the axons were counted within this region; and the density to square millimeters was calculated. Furthermore, the diameters of the axons and cell bodies, the number of cells with multi-lobular nuclei, and cells showing myelination were examined in the same standardized region. Measurements and counts were obtained from five sections per rat, and five rats (n=5) were analyzed for each experimental condition. All variances represent standard error (±SEM).

Figure 1A:
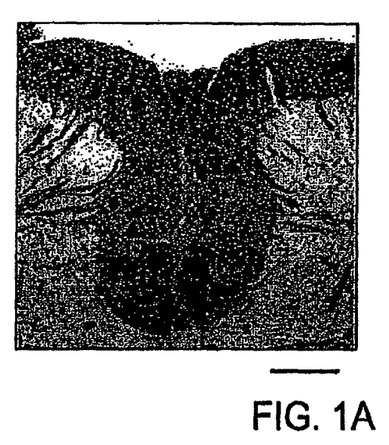
Figure 1B:
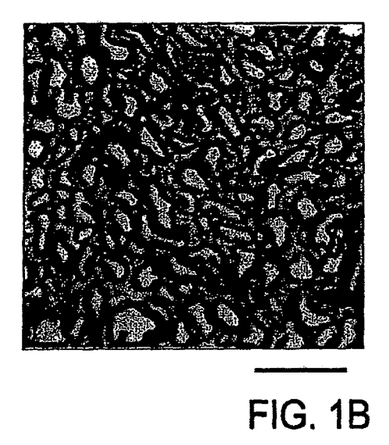
Figure 1C:
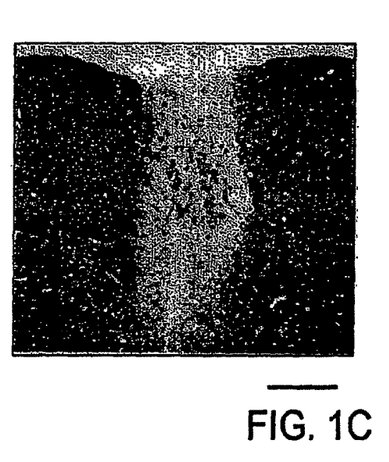
Figure 1D:
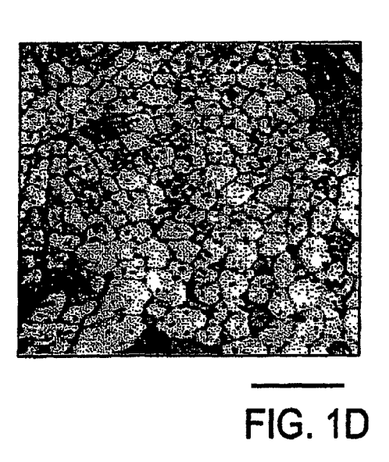

The dorsal column in the spinal cord mostly consists of myelinated axons (FIG. 1A, B). The proliferation of endogenous glial cells was inhibited by the irradiation of X-ray to the dorsal columns of the lumbar spinal cord. Further, by the administration of a nucleic acid chelator, ethidium bromide, glial cells such as oligodendrocytes were found damaged and local demyelination occurred. Such lesions generated according to this procedure are characterized by almost complete loss of endogenous glial cells (astrocytes and oligodendrocytes) and preservation of axons (FIG. 1C). Examination of the lesion with a light microscope under a higher magnification revealed that congested areas consisting of demyelinated axons are appositioned closely to one another separated by areas wherein the debris of myelin exist and wherein macrophages exist (FIG. 1D). The lesion occupied nearly the entire dorso-ventral extent of the dorsal columns 5 to 7 mm longitudinally. Almost none of the endogenous invasion of Schwann cells or astrocytes occurs till the sixth to eighth week. With the start of invasion, these glial cells begin to invade into the lesion from peripheral borders. Thus, a demyelinated and glial-free environment is present for at least 6 weeks in vivo.

Figure 2A:
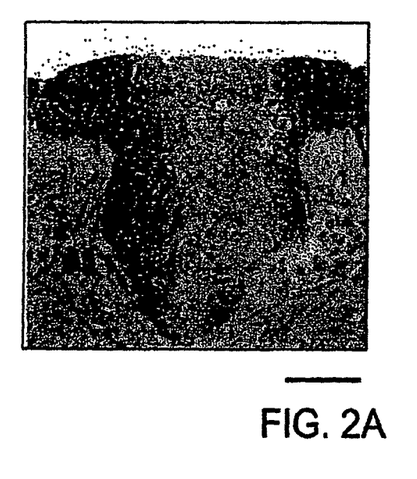
Figure 2B:
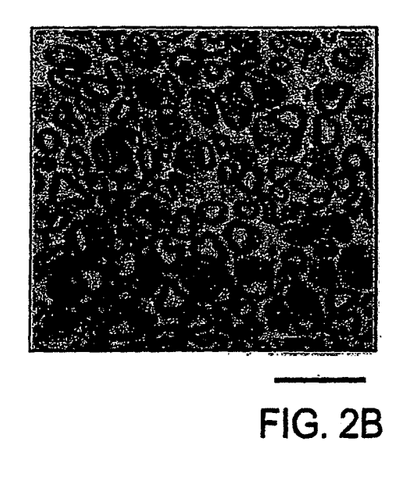
Figure 2C:
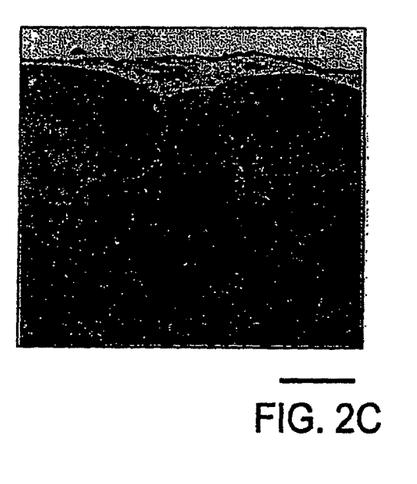
Figure 2D:
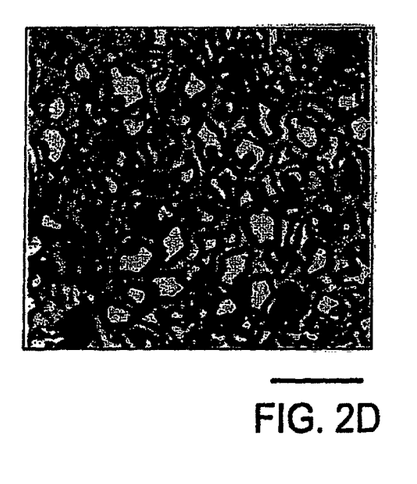

Three weeks after transplantation of LacZ transgenic mouse bone marrow cells (BM) into the central region of the lesion in immunosuppressed and demyelinated rat models, extensive remyelination of the demyelinated axons was observed (FIGS. 2A and 2B). Remyelination was observed across the entire coronal dimension of the dorsal columns and throughout the antero-posterior extent of the lesion. FIGS. 2C and 2D show the pattern of remyelination observed after transplantation of allogeneic Schwann cells (SC) into the EB-X lesion model. It is remarkable that large nuclear and cytoplasmic regions were found around the remyelinated axons, a characteristic of peripheral myelin, by both BM and SC transplantations.

EXAMPLE 4

Detection of β-Galactosidase Reaction Products In Vivo

Three weeks after transplantation, β-galactosidase expressing myelin-forming cells were detected in vivo. Spinal cords were collected and fixed in 0.5% glutaraldehyde in phosphate-buffer for 1 h. Sections (100 μm) were cut with a vibratome and β-galactosidase expressing myelin-forming cells were detected by incubating the sections at 37° C. overnight with X-Gal (substrate which reacts with β-galactosidase to develop color) at a final concentration of 1 mg/ml in X-Gal developer (35 mM $K_3Fe(CN)_6$/35 mM $K_4Fe(CN)_6$·$3H_2O$/2 mM $MgCl_2$ in phosphate-buffered saline) to form blue color within the cell. Sections were then fixed for an additional 3 h in 3.6% (vol/vol) glutaraldehyde in phosphate-buffer (0.14 M), and were examined with light microscope for the presence of blue reaction product (β-galactosidase reaction product). Prior to embedding in EPON, the tissue was treated with 1% $OsO_4$, dehydrated in a graded series of ethanol, and soaked in propylene oxide for a short period. Ultrathin sections were then examined under an electron microscope without further treatment.

Figure 3A:
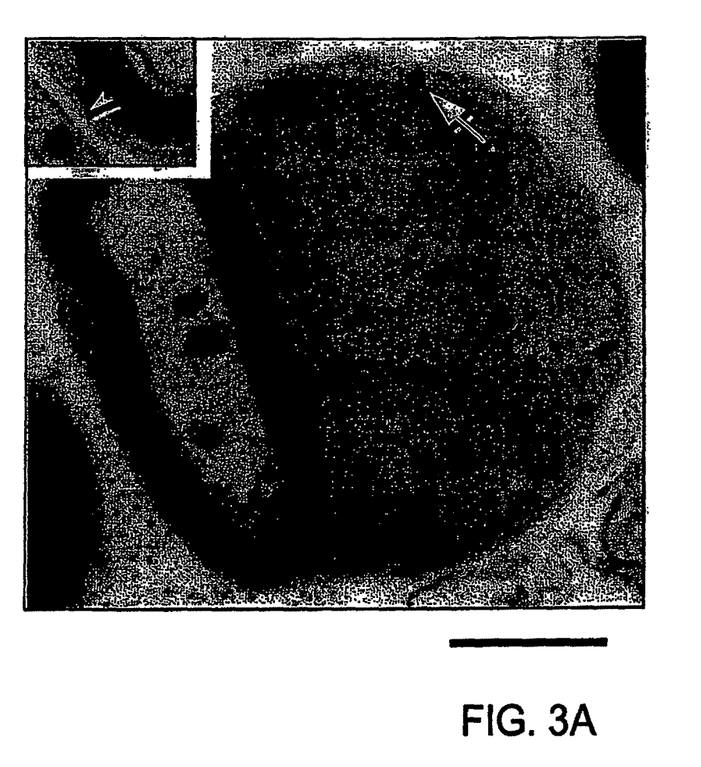

Under the electron microscope, most of the myelin-forming cells derived from donor cells retained the basal membrane (FIG. 3: wedge-shaped mark). Additionally, the myelin-forming cells had relatively large nucleus and cytoplasm, which suggests the formation of a peripheral nervous system-type myelin sheath.

It was confirmed that almost no endogenous remyelination by oligodendrocytes or Schwann cells occurs for at least six weeks in the lesion model used in the present experiment. Furthermore, the donor cells that contained the reporter gene LacZ, i.e., X-Gal-positive cells, were observed to form myelin at the electron microscopic level (FIG. 3: arrow).

Differentiation into neurons and glial cells could be observed following the transplantation of bone marrow cells into the EB-X lesions, but not by SC transplantation. Five percent of lacZ-positive cells (transplanted bone marrow cells) in the EB-X lesions showed NSE (Neuron Specific Enolase)-immunoreactivity and 3.9% showed GFAP (Glial Fibrially Acidic Protein)-immunoreactivity, indicating that some of the bone marrow cells can differentiate into neurons or glial cells, respectively, in vivo.

Furthermore, employing antibodies, the present inventors isolated mesenchymal stem cells with the characteristic of cell markers SH2 (+), SH3 (+), CD29(+), CD44 (+), CD14 (−), CD34 (−), and CD45 (−) from the cell fraction obtained in Example 1 (1). Furthermore, they discovered that transplantation of the cells into the demyelinated regions of rat spinal cord results in more efficient remyelination. It was also revealed that the cells survived favorably and differentiated into neurons or neuronal cells and glia cells when transplanted into cerebral infarction model rats.

Further, the present inventors isolated stromal cells characterized by the cell surface markers Lin (−), Sca-1 (+), CD10 (+), CD11D(+), CD44(+), CD45(+), CD71(+), CD90(+), CD105(+), CDW123(+), CD127(+), CD164(+), fibronectin (+), ALPH(+), and collagenase-1(+) from the cell fraction obtained in Example 1 (1). Transplantation of the cells into demyelinated regions of rat spinal cord also resulted in efficient remyelination.

Further, the present inventors isolated cells characterized by the cell surface marker AC133 (+) from the cell fraction obtained in Example 1 (1). Transplantation of the cells into demyelinated regions of rat spinal cord also resulted in efficient remyelination.

In addition, the present inventors obtained a cell fraction containing AC133-positive cells capable of differentiating into neural cells from rat embryonic hepatic tissues by the following procedure. Specifically, first, liver tissues collected from rat fetuses were washed in L-15 solution, and then treated enzymatically in L-15 solution containing 0.01% DNaseI, 0.25% trypsin, and 0.1% collagenase at 37° C. for 30 minutes. Then, the tissue was dispersed into single cells by pipetting several times. The single-dispersed embryonic hepatic tissues were centrifuged as in Example 1 (1) (preparation of mononuclear cell fraction from femur) to isolate a mononuclear cell fraction. The obtained mononuclear cell fraction was washed, and then, AC133(+) cells were recovered from the cell fraction using anti-AC133 antibody. The isolation of AC133-positive cells can be achieved using magnetic beads or a cell sorter (FACS or the like). Transplantation of the obtained AC133-positive cells into demyelinated regions of rat spinal cord also resulted in efficient remyelination.

Industrial Applicability

As described above, the present invention provides fractions of mononuclear cells isolated and purified by collecting bone marrow-derived bone marrow cells, cord blood-derived cells, or fetal liver-derived cells. Transplantation of such mononuclear cell fractions into a demyelination model animal was confirmed to result in remyelination of the demyelinated axon.

Cells for transplantation can be relatively easily isolated from a small quantity of bone marrow cell fluid aspirated from bone marrow, and can be prepared for transplantation in several tens of minutes after the cells are being collected. Thus, these cells can serve as useful and regenerable cellular material for autotransplantation in the treatment of demyelinating diseases.

This invention highlights the development of the autotransplantation technique to treat demyelinating diseases in the central nervous system. Furthermore, the use of the present invention in transplantation and regeneration therapy for more general and diffuse damage in the nervous system is envisaged. In other words, this invention sheds light on autotransplantation therapy against ischemic cerebral damage, traumatic cerebral injury, cerebral degenerating diseases, and metabolic neurological diseases in the central and peripheral nervous systems.

According to the present invention, cells in the hematopoietic system (bone marrow or cord blood) are used as donor cells. Thus, to treat neurological diseases, the cells may be transplanted into the vessels instead of directly transplanting them into neural tissues. Specifically, donor cells transplanted into a vessel can migrate to the neural tissues and thereby regenerate the neural tissues. Hence, the present invention is a breakthrough in developing a therapeutic method for relatively noninvasive transplantation.

Furthermore, the present invention adds significantly to elucidate the mechanism underlying the differentiation of non-neural cells such as hematopoietic cells and mesenchymal cells into neural cells. When genes determining the differentiation are identified and analyzed, use of such genes will allow efficient transformation of a sufficient quantity of non-neural cells such as hematopoietic cells and mesenchymal cells in a living body to neural cells. Thus, the present invention is a breakthrough in the field of "gene therapy" for inducing regeneration of neural tissues.

What is claimed is:
1. A method for transplanting an isolated cell population into a patient with a brain tumor comprising:
    injecting into the patient an isolated cell population comprising cells having surface markers SH2(+), SH3(+), SH4(+), CD29(+), CD44(+), CD14(−), CD34(−), and CD45(−), wherein the isolated cell population is prepared by a method comprising:
diluting bone marrow cells; and
isolating the cell population from a mononuclear cell fraction of the bone marrow cells.

2. The method according to claim 1, wherein said isolated cell population is injected intravenously.

3. The method according to claim 1, wherein said isolated cell population is injected intra-arterially.

4. The method according to claim 1, wherein said isolated cell population is injected into the carotid artery.

5. A method for transplanting an isolated cell population into a patient with a brain tumor comprising:
injecting into the patient an isolated cell population comprising cells having surface markers SH2(+), SH3(+), SH4(+), CD29(+), CD44(+), CD14(−), CD34(−), and CD45(−),
wherein the isolated bone marrow cell population is prepared by a method comprising:
diluting cord blood cells; and
isolating the cell population from a mononuclear cell fraction of the cord blood cells.

6. The method according to claim 5, wherein said isolated cell population is injected intravenously.

7. The method according to claim 5, wherein said isolated cell population is injected intra-arterially.

8. The method according to claim 5, wherein said isolated cell population is injected into the carotid artery.

* * * * *